United States Patent
Swartz et al.

(10) Patent No.: US 7,628,920 B2
(45) Date of Patent: Dec. 8, 2009

(54) COMPOSITIONS AND METHODS FOR SEPARATING ENANTIOMERS

(75) Inventors: Michael Swartz, Uxbridge, MA (US);
Uwe Dieter Neue, Ashland, MA (US);
Peter G. Alden, Whitinsville, MA (US);
Falk-Thilo Ferse, Berlin (DE)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 10/599,583

(22) PCT Filed: Apr. 6, 2005

(86) PCT No.: PCT/US2005/011526

§ 371 (c)(1),
(2), (4) Date: Mar. 28, 2008

(87) PCT Pub. No.: WO2005/099855

PCT Pub. Date: Oct. 27, 2005

(65) Prior Publication Data

US 2008/0237130 A1    Oct. 2, 2008

Related U.S. Application Data

(60) Provisional application No. 60/560,070, filed on Apr. 7, 2004.

(51) Int. Cl.
*B01D 15/08* (2006.01)
(52) U.S. Cl. ............ 210/635; 210/656; 210/196.2
(58) Field of Classification Search .......... 210/635, 210/656, 659, 198.2, 502.1
See application file for complete search history.

(56) References Cited

U.S. PATENT DOCUMENTS

| | | | | |
|---|---|---|---|---|
| 4,290,893 A * | 9/1981 | Hare et al. | ................ | 210/656 |
| 4,512,898 A * | 4/1985 | Oi et al. | ................ | 210/656 |
| 4,565,877 A * | 1/1986 | Wada et al. | ................ | 548/530 |
| 4,696,745 A * | 9/1987 | Itagaki et al. | ............ | 210/502.1 |
| 4,767,670 A * | 8/1988 | Cox et al. | ................ | 428/403 |
| 5,078,886 A * | 1/1992 | Hsu | ................ | 210/632 |
| 5,338,454 A | 8/1994 | Duff | | |
| 6,090,250 A | 7/2000 | Mazzeo et al. | | |
| 6,224,775 B1 * | 5/2001 | Foley et al. | ................ | 210/635 |
| 6,277,782 B1 * | 8/2001 | Moller et al. | ................ | 502/402 |
| 6,289,286 B1 * | 9/2001 | Andersson et al. | ............ | 702/19 |
| 6,420,181 B1 * | 7/2002 | Novak | ................ | 436/104 |
| 7,125,492 B2 * | 10/2006 | Bidlingmeyer et al. | ...... | 210/635 |
| 7,314,550 B2 * | 1/2008 | Warner et al. | ............ | 210/198.2 |
| 2002/0050476 A1 * | 5/2002 | Ma et al. | ................ | 210/638 |
| 2004/0159610 A1 * | 8/2004 | Armstrong | ................ | 210/656 |
| 2005/0011836 A1 * | 1/2005 | Bidlingmeyer et al. | ...... | 210/656 |

(Continued)

OTHER PUBLICATIONS

Pettersson, Journal of Chromatography, 435 (1988), pp. 225-228.*

*Primary Examiner*—Ernest G Therkorn
(74) *Attorney, Agent, or Firm*—Anthony J. Janiuk

(57) ABSTRACT

A liquid chromatography system comprising a chiral mobile phase used to separate enantiomeric molecules present in a sample is disclosed herein. In one aspect, the mobile phase comprises a chiral solvent. In another aspect, the mobile phase includes a chiral solvent but also a buffering agent. The liquid chromatography system described herein includes both high pressure liquid chromatography (HPLC) as well as high pressure capillary liquid chromatography (CapLC).

8 Claims, 1 Drawing Sheet

U.S. PATENT DOCUMENTS

2005/0092686 A1* 5/2005 Li .............................. 210/656
2006/0118490 A1* 6/2006 Landry et al. ............... 210/656
2007/0056908 A1* 3/2007 Peyrin et al. ................ 210/656
2007/0144968 A1* 6/2007 Fazioni et al. ............... 210/635

* cited by examiner

COMPOSITIONS AND METHODS FOR SEPARATING ENANTIOMERS

CROSS REFERENCE RELATED APPLICATION INFORMATION

This application is a 371 of PCT/US2005/011526, filed Apr. 6, 2005, which in turn, claims priority from U.S. Provisional Patent Application No. 60/560,070, filed Apr. 7, 2004. The contents of these applications are incorporated herein by reference.

FIELD OF THE INVENTION

The present invention relates to the separation of enantiomers. More specifically, the instant invention pertains to compositions and methods of employing a chiral mobile phase that effectuates the separation of enantiomers.

BACKGROUND OF THE INVENTION

The separation of enantiomers is considered to be one of the more difficult tasks faced by practitioners of analytical chemistry. Chiral separations are one of the most challenging types of purification because of the extreme similarity between the two components in a racemic mixture. Each component is a mirror image of the other. These chiral components exhibit identical physical properties in non-chiral environments. As a result, conventional separation technology such as gas chromatography, liquid chromatography and capillary electrophoresis have been modified to provide a chiral environment.

Different approaches to providing a chiral environment have been attempted. Chiral stationary phases have been developed. These are chromatography columns with chiral functional groups that interact with the analytes. Additives can be added to a mobile phase creating a mobile phase that has chiral selectivity. Sometimes these chiral stationary phases are used in conjunction with a chiral mobile phase with mixed results. One problem with such an approach is the instability of the column. Additionally, commercial additives can be cost-prohibitive, especially at the analytical scale.

Chiral separations have been accomplished using a variety of techniques. Over the last thirty years investigators have shown that chiral separations are possible using gas chromatography (GC), liquid chromatography (LC), gel electrophoresis, paper electrophoresis, and capillary electrophoresis (CE). These separations are based on the ability of the enantiomers of the sample to differentially interact with a chiral phase that is part of the separation system.

The chiral phase can be embodied in a variety of ways. In chromatography, the chiral phase is conventionally part of the stationary phase, or column. In both GC and LC, a wide variety of chiral columns are available. The adsorption of the enantiomers by the stationary phase is the sum of both achiral and chiral interactions. The achiral interactions might include ionic, hydrogen bonding, and hydrophobic adsorption. The chiral interactions are derived from the spatial relationship of the achiral interactions. The energy difference contributed by this chiral interaction is the basis for the chiral separation.

The efficiency of the current generation of chiral chromatographic systems is generally low, thus the difference in the free energy of the interaction between the chiral modifier and the enantiomers must be relatively large in order to gain adequate resolution. This large energy difference requirement contributes to the low efficiency of many chiral HPLC systems (5000 to 10000 plates), and the tailing peaks observed on many chiral columns. This large energy difference requirement also prevents chiral HPLC columns from being of general use. Currently, chiral HPLC columns are selective for small classes of compounds, so more than fifty chiral phases have been commercialized. In this environment, method development is highly empirical and very tedious. There is a need to create systems which separate larger classes of enantiomers or provide easier method development.

Currently, there exists a need to develop cost-effective chiral mobile phases that can effectively facilitate the separation of enantiomers. Optimally, these mobile phases comprise chiral solvents and not merely additives.

SUMMARY OF INVENTION

The present invention relates to the separation of enantiomers. More specifically, the instant invention pertains to compositions and methods of employing a chiral mobile phase that effectuates the separation of enantiomers.

According to the present invention, a separation system comprising a stationary phase and a chiral mobile phase is used for separating analytes contained in an enantiomeric mixture. In this embodiment, the stationary phase can be a conventional chromatography column. In this embodiment, the chiral mobile phase comprises a chiral solvent. In one aspect, the chiral mobile phase also comprises a buffering agent. In one aspect, the separation system is a liquid chromatography system. The liquid chromatography system of the present invention includes both high pressure liquid chromatography (HPLC) as well as high pressure capillary liquid chromatography (CapLC).

According to the present invention, a method comprising a separation system and a chiral mobile phase is used to separate analytes present in an enantiomeric sample. In this embodiment, the separation system can be a liquid chromatography system. This system includes both HPLC and CapLC. The method involves employing a chiral mobile phase together with a stationary phase. The stationary phase can be a conventional chromatography column.

DETAILED DESCRIPTION

Figure 1:
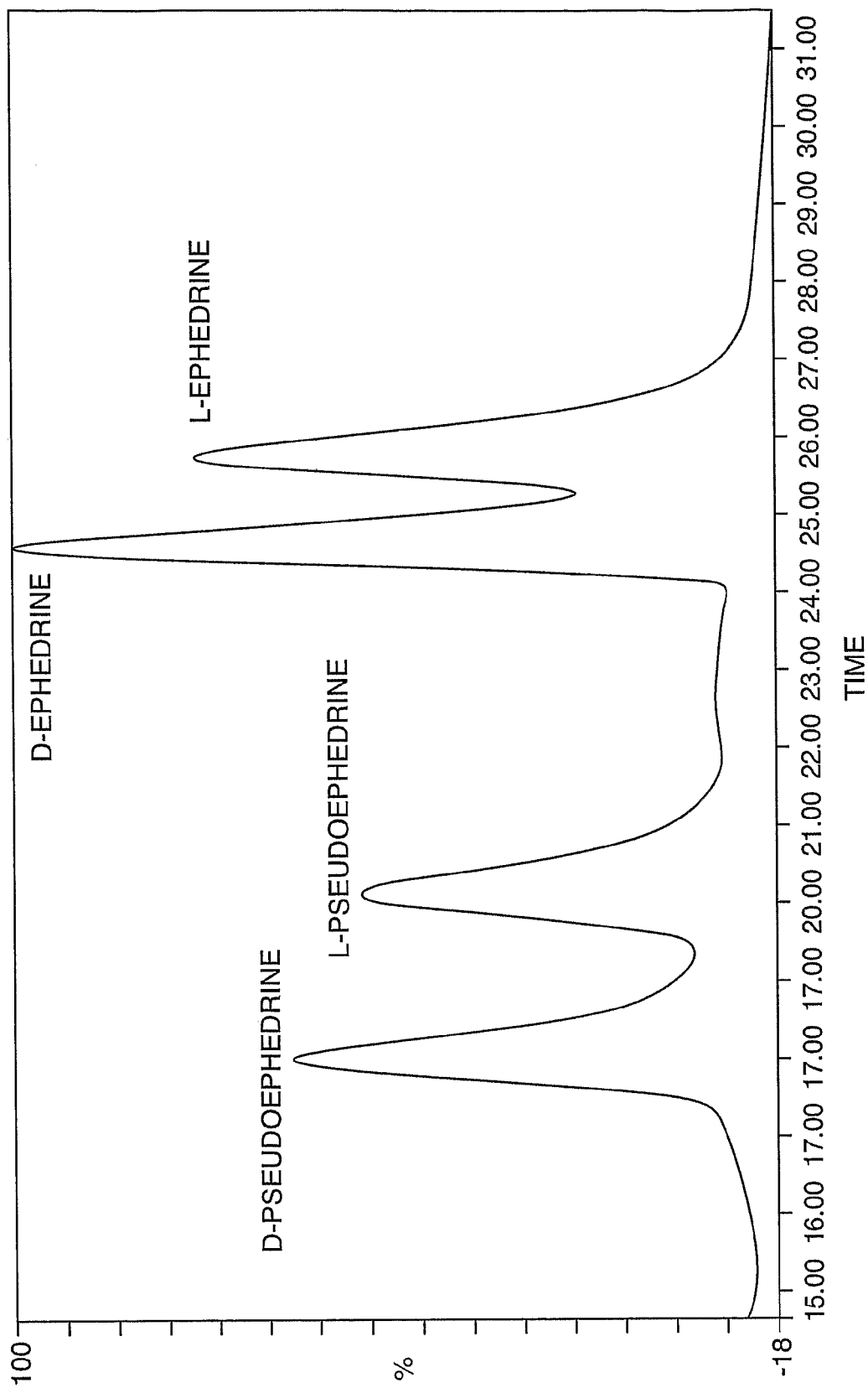
FIG. 1 is a chromatogram showing the separation of the enantiomers (D,L) Pseudoephedrine and (D,L) ephedrine using a composition of the present invention.

The present invention relates to the separation of enantiomers. More specifically, the instant invention pertains to compositions and methods of employing a chiral mobile phase that effectuates the separation of enantiomers.

In one embodiment of the present invention, a separation system comprising a stationary phase and a chiral mobile phase is used for separating analytes contained in an enantiomeric mixture. In this embodiment, the stationary phase can be a conventional chromatography column. In this embodiment, the chiral mobile phase comprises a chiral solvent. In one aspect, the chiral mobile phase also comprises a buffer agent. In one aspect, the separation system is a liquid chromatography system. The liquid chromatography system of the present invention includes both high pressure liquid chromatography (HPLC), ultra or very high pressure HPLC (>5000 psi up to and exceeding 50,000 psi), as well as high pressure capillary liquid chromatography (CapLC).

In another embodiment of the present invention, a method comprising a separation system and a chiral mobile phase is used to separate analytes present in an enantiomeric sample. In this embodiment, the separation system can be a liquid chromatography system. This system includes both HPLC and CapLC. The method involves employing a chiral mobile phase together with a stationary phase. The stationary phase can be a conventional chromatography column.

When employing separation technology, in particular liquid chromatography, to chiral separation, typically the stationary phase (or column) possesses chiral selectivity. However, chiral selectivity is not the exclusive realm of the stationary phase. Mobile phases can possess chiral selectivity by the addition of an additive or modifier. See U.S. Pat. No. 6,090,250 to Mazzeo et al., the entire teaching of which is incorporated herein by reference.

The present invention pertains to a mobile phase that has chiral selectivity. In one aspect, the mobile phase comprises a chiral solvent. This significantly differs from conventional chiral mobile phases that obtain their chiral selectivity by having a chiral additive added thereto. In the instant invention, the mobile phase itself possesses chiral selectivity. The mobile phase can have one or more buffering agents added to it for maintenance of pH.

There are some advantages of using a chiral mobile phase as opposed to employing chiral additives. For example, using a chiral mobile phase provides for sensitivity in detecting the analytes of interest. The low noise to signal ratio promotes greater sensitivity for detection. Also, there is typically a lower viscosity associated with using a chiral mobile phase, thus allowing faster flow rates, higher throughput, better efficiency, higher peak capacity and resolution. Additionally, the use of chiral mobile phases involves a single separation mechanism, one less interaction when compared with employing additives resulting in better resolution and peak efficiency. Also, both enantiomers are available for peak order reversal which is not always the case when using chiral additives.

The chiral mobile phase of the present invention is directed to a chiral molecule having the general formula:

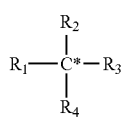

wherein $R_1$-$R_4$ are all different providing for a chiral center, i.e., C* is an asymmetrical carbon; the R groups can be a combination of any other chemical moiety, again with the limitation that the C* carbon remains the only chiral center, examples of R groups include, but are not limited to, hydrogen, alkanes, alkenes, alkyl groups for example $C_1$-$C_{24}$ and greater, aryl, arylalkyl, hydroxyl, halogens, esters, ethers, alcohols, saturated and/or unsaturated hydrocarbons, branched and/or unbranched hydrocarbons, amines, amidines, amides, ketone, acetone, dienes, carboxyl, sulfhydrals, sulfates, sulfonates, sulfur, enols, and alike and combinations thereof.

All chiral compounds must have at least one chiral center. A chiral molecule is one that rotates a plane of polarized light. A chiral molecule is defined as not being superimposable on its mirror image. One important aspect about this invention is that by selecting "R" or "S" mobile phases one can manipulate the elution order of chiral analytes. The "R" and "S" terminology simply refer to whether a particular molecular configuration rotates light to the right or left, respectively.

Preferably, the chiral mobile phase comprises from about 70% to about 100% "R" or "S." More preferably, the chiral mobile phase comprises about 85% to about 100% "R" or "S." Even more preferably, the chiral mobile phase comprises from about 90% to about 100% "R" or "S." Most preferably, the chiral mobile phase comprises from about 95% to about 100% "R" or "S."

Examples of chiral mobile phases include, but are not limited to, 2-butanol, 2-butylamine, 3-amino-1,2-propanediol, 1-amino-2-propanol, 2-amino-1-propanol, 1-dimethylamino-2-propanol, 1,2-propanediol, propylene carbonate, 1,2-diaminopropane dihydrochloride, 1-methyl-2-pyrrolidone, methyl-2-pyrrolidone-5-carboxylate, 1,2-dichloropropane, 2-bromopropionic acid, 2-bromopropionitrile, 2-chloropropionic acid, 2-chloropropionitrile, epichlorohydrin, 3-chloro-2-methylpropionitrle, 1-bromo-3-chloro-2-methylpropane, propylene oxide, 1,2-propanediol diacetate, 1-methoxy-2-propanol, 1-methoxy-2-propanol acetate, 1,2-diamino propane, 3-aminopyrrolidine, 4-chloro-3-hydroxy butyronitrile, 1-chloro-2-propanol, 2-chloro-1-propanol, methyl-2,3-dichloropropionate, 2-butanol, 1,2,4-butanetriol, 1,3-butanediol, 2,3-butanediol, β-hydroxy-γ-butyrolactone, 3-chloro-2-butanone, 4-chloromethyl-2,2-dimethyl-1,3-dioxolane, 1-chloro-2-methylbutane, methyl-2-chloropropionate, and 3-hydoxy pyyrolidine, and combinations thereof.

In addition to the chiral agent, the chiral mobile phase of the present invention can also comprise a buffering agent. The buffering salt does not contribute to the chiral selectivity of the mobile phase, rather, it provides buffering capacity for it. Therefore, the chiral mobile phase of the instant invention not only possesses chiral selectivity but also, can maintain pH through its buffering capacity.

The present invention increases the flexibility in choosing which liquid chromatography column to use for chiral separations. Because the mobile phase itself possesses chiral selectivity, the choice of columns extend beyond chiral columns. Therefore, practitioners can use columns that are normally associated with non-chiral separations, for example, a $C_{18}$ reverse-phase column.

An emerging area of chromatographic separation and analysis is developing around the use of capillary columns. Such columns have diameters typically in the range of 30 to 800 micron internal diameter. These columns can be packed with a particulate packing material, or in the smallest diameter range, the stationary phase can be provided by the column wall itself or a coating applied to that wall. Mobile phase flow rates for such particulate packed capillary columns can typically range from approximately one nanoliter per minute to ten or more microliters per minute. These figures represent a three to six order-of-magnitude reduction in flow rate and consequently a similar reduction in the volume of the separation from what is currently practiced on, for example, the four millimeter internal diameter columns widely commercially available.

HPLC systems designed around capillary columns have particular utility when the HPLC separation is coupled with a downstream process that does not readily tolerate large amounts of HPLC mobile phase, or where the use of unusually expensive mobile phases is desired. Examples of such processes are: (1) chiral separation of enantiomers, (2) infrared spectroscopy, where organic solvents used for HPLC must be eliminated because they represent an interference to analyte detection in the infrared region of the electromagnetic spectrum, (3) microfraction collection, which requires that the analyte be deposited in a small volume on a collection substrate with minimum associated background contamination from the HPLC mobile phase, (4) nuclear magnetic resonance spectroscopy (NMR) which can benefit from significant signal background reduction through the use of somewhat exotic mobile phases, such as deuterium-substituted mobile phases in the case of proton-NMR, and (5) mass spectrometry, which requires that the sample reside in the gas phase at high vacuum conditions prior to mass analysis.

Substantially, the same requirements for precision and accuracy of solvent composition and flow rate delivery exist as for larger scale chromatography, but the mechanisms for controlling delivery must function at approximately one one-thousandth or less of the conventional volume scale. In particular, the non-idealities of a given implementation which could be dismissed at a much larger volumetric scale give rise to overwhelmingly large perturbations to a system of the scale of capillary HPLC.

Interest has developed in the ability to perform HPLC separations using extremely small diameter packing materials, that is, less than three micron diameter, with concomitantly high mobile phase pressure, which is required to drive the liquid through a bed filled with such packing particles. Enhanced separation characteristics of HPLC are demonstrated, in particular, either the absolute peak capacity of the separation, or the throughput of the separation as expressed in peaks eluted per unit time, can be substantially improved through the correct use of small packing particles and a high system pressure. The utility of particles as small as one micron diameter and system pressures in the rage of 10,000 to 100,000 PSIG has been demonstrated.

In using such small diameter columns (30 to 75 micron internal diameter), the actual volume of separation becomes exceedingly small, given that the mobile phase flow rates are typically in the 5 to 200 nanoliter per minute range. Gradient formation requires that the individual components of the mobile phase must be delivered at levels as low as 0.1% of the total system flow rate. In addition, high-pressure gradient formation pumps must deliver the component flows in a manner which is reproducible in fashion, against the full system operating pressure, without perturbations. The above described analytical requirements imply the ability to quantitatively deliver component flow rates as small as 10 picoliters per minute against pressures as high as 100,000 PSIG.

The present invention also pertains to methods for separating analytes contained within a sample. In one aspect, the analytes of the sample comprise one or more enantiomeric molecules. The present methods include an aqueous phase comprised of a chiral mobile phase of the instant invention. The aqueous phase can also include a buffering agent in order to provide pH control for the aqueous phase.

Typically, the sample is admixed with an organic solvent, such as methanol or acetonitrile. This admixture is then introduced into a means for separation. The means for separation include, but not limited to, a liquid chromatography, a capillary liquid chromatography, supercritical fluid chromatography, gas chromatography, and alike.

The means for separation is equilibrated using a chiral mobile phase of the present invention. As the analytes are introduced into the separation means they will form an admixture with the mobile phase traversing the separation system.

The means for separation typically includes a stationary phase, perhaps in the form of a chromatography column. Columns have an interior chamber usually comprising a stationary phase that is made up of functional chemical groups. For example, these functional groups can be an alkyl group that provides a hydrophobic environment as in a $C_{18}$ column. All molecules have a hydrophobic profile. Typically, molecules having a higher hydrophobic profile will in turn have a higher affinity for the hydrophobic functionality of the stationary phase. This, then, contributes to the elution order of analytes. However, where the analytes of interest are enantiomers, their elution profile is also dependent upon the chiral selectivity of the mobile phase.

As the analytes elute the stationary phase, one or more detection systems can be used to ascertain the eluted analyte. These detections systems include, but are not limited to, mass spectrometry, nuclear magnetic resonance, ultra-violet, refractive index, infrared spectroscopy, fluorescence, photodiode array, evaporative light scattering, conductance, and nitrogen/sulphur specific detectors.

In one aspect, the elution order of the analytes can be altered by manipulating the mobile phase. In one aspect, the elution order of enantiomeric analytes are altered by changing the mobile phase's selectivity. For example, a mobile phase comprising around 95% "R" can be switch to comprise around 95% "S" thereby changing the selectivity of the chiral mobile phase. The ability to switch elution order by manipulating the mobile phase composition is important because it is desirable that any trace enantiomeric impurity elutes before the often tailed, larger peak of the opposite enantiomer so that it can be detected and more accurately quantified. Conversely, in the case of fronted peaks, it is desirable that the trace enantiomer elutes last. By having both "R" and "S" mobile phases available, the mobile phase can be "tuned" for the desirable elution order.

The present invention includes both isocratic and gradient methods. In an isocratic method, the equilibrating and eluting mobile phases are the same and remain constant through the entire process of separation. A separation method that includes a gradient profile employs two or more mobile phases. For example, a sample contained within a solvent like methanol can be introduced into a means for separation and over time a chiral mobile of the present invention can be introduced and increased over time, thereby increasing the presence of the chiral mobile phase within the aqueous phase. There can also be combinations of isocratic and gradient elution profiles within a single separation procedure. Optimization of the aqueous phase profile (i.e., isocratic, gradient or a combination thereof) can be accomplished readily by one skilled in the art.

EXAMPLE

FIG. 1 illustrates a chromatogram obtained from the separation of enantiomeric molecules (d, l) pseudoephedrine and (d, l) ephedrine using a chiral mobile of the present invention. The column employed for this separation was the 3.5 µm, 0.32 mm×150 mm Xterra RP18 (a reverse-phase $C_{18}$ column). The flowrate was set at 5.0 µL/min. The column temperature was set at 25° C. The sample volume that was injected was 1.0 L (20 ng). Two solvents were employed. Eluent A comprised 25 mM s-Dodecylcarbonylvaline (s-DDCV) with 5% THF (pH 7.0), and eluent B was 25 mM s-DDCV with 5% THF (pH 11.0). A gradient method was employed where initial conditions were 15% eluent B and over thirty minutes eluent B was 85%.

In FIG. 1, the separation of two enantomeric pairs is clearly discernable using a chiral mobile solvent.

While this invention has been particularly shown and described with references to specific embodiments, it will be understood by those skilled in the art that various changes in form and details may be made therein without departing from the spirit and scope of the invention as defined by the appended claims.

What is claimed is:

1. A method of separating analytes contained within a sample, wherein said sample has one or more enantiomeric analytes, comprising:

providing a reagent having a chiral mobile phase with the formula:

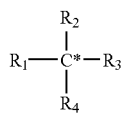

wherein
$R_1$-$R_4$ are all different, and wherein the individual R group is selected from the group consisting of hydrogen, alkanes, alkenes, alkyl groups for example $C_1$-$C_{24}$ and greater, aryl, arylalkyl, hydroxyl, halogens, esters, ethers, alcohols, saturated and/or unsaturated hydrocarbons, branched and/or unbranched hydrocarbons, amines, amidines, amides, ketone, acetone, dienes, carboxyl, sulfhydrals, sulfates, sulfonates, sulfur, enols, and combinations thereof wherein said chiral mobile phase is selected from the group consisting of 2-butanol, 2-butylamine, 3-amino-1,2-propanediol, 1-amino-2-propanol, 2-amino-1-propanol, 1-dimethylamino-2-propanol, 1,2-propanediol, propylene carbonate, 1,2-diaminopropane dihydrochloride, 1-methyl-2-pyrrolidone, methyl-2-pyrrolidone-5-carboxylate, 1,2-dichloropropane, 2-bromopropionic acid, 2-bromopropionitrile, 2-chloropropionic acid, 2-chloropropionitrile, epichlorohydrin, 3-chloro-2-methylpropionitrle, 1-bromo-3-chloro-2-methylpropane, propylene oxide, 1,2propanediol diacetate, 1-methoxy-2-propanol, 1-methoxy-2-propanol acetate, 1,2-diamino propane, 3-aminopyrrolidine, 4-chloro-3-hydroxy butyronitrile, 1-chloro-2-propanol, 2-chloro-l-propanol, methyl-2,3-dichloropropionate, 2-butanol, 1,2,4-butanetriol, 1,3-butanediol, 2,3-butanediol, β-hydroxy-γ-butyrolactone, 3-chloro-2-butanone, 4-chloromethyl-2,2-dimethyl-1,3-dioxolane, 1-chloro-2-methylbutane, methyl-2-chloropropionate, and 3-hydoxy pyrrolidine; introducing said sample into a means for separation; and contacting said sample with said chiral mobile phase resulting in an admixture.

2. The method of claim 1 further comprising the step of detecting one or more analytes of interest.

3. The method of claim 2, wherein said detection is accomplished using mass spectrometry, nuclear magnetic resonance, ultra-violet, refractive index, infrared spectroscopy, fluorescence, photodiode array, evaporative light scattering, conductance, and nitrogen/sulphur specific detectors.

4. The method of claim 1, wherein said analytes elution order is reversed by manipulating said chiral mobile phase.

5. The method of claim 1, wherein said aqueous phase further comprises a buffering agent.

6. The method of claim 1, wherein said means for separation is selected from the group comprising liquid chromatography and capillary liquid chromatography.

7. The method of claim 1, wherein an isocratic elution method is employed for separating said analytes.

8. The method of claim 1, wherein a gradient elution method is employed for separating said analytes.

* * * * *